United States Patent [19]

Burton et al.

[11] Patent Number: 5,026,377
[45] Date of Patent: Jun. 25, 1991

[54] STENT PLACEMENT INSTRUMENT AND METHOD

[75] Inventors: John H. Burton; Bradford G. Staehle, both of Minnetonka, Minn.

[73] Assignee: American Medical Systems, Inc., Minnetonka, Minn.

[21] Appl. No.: 569,267

[22] Filed: Aug. 17, 1990

Related U.S. Application Data

[63] Continuation of Ser. No. 379,458, Jul. 13, 1989, abandoned.

[51] Int. Cl.⁵ .............................................. A61B 17/00
[52] U.S. Cl. .................................................. 606/108
[58] Field of Search ................ 606/108, 198, 200, 191

[56] References Cited

U.S. PATENT DOCUMENTS

| | | | |
|---|---|---|---|
| 4,553,545 | 11/1985 | Maass et al. | 606/198 |
| 4,580,568 | 4/1986 | Gianturco . | |
| 4,655,771 | 4/1987 | Wallsten . | |
| 4,681,110 | 7/1987 | Wiktor . | |
| 4,732,152 | 3/1988 | Wallsten et al. | 606/108 |
| 4,733,665 | 3/1988 | Palmaz | 606/108 |
| 4,768,507 | 9/1988 | Fischell et al. . | |
| 4,830,003 | 5/1989 | Wolff et al. | 606/191 |
| 4,913,141 | 4/1990 | Hillstead | 606/108 |

Primary Examiner—Michael H. Thaler
Attorney, Agent, or Firm—Peter C. Richardson; Lawrence C. Akers; Mark Dryer

[57] ABSTRACT

An instrument for the deployment or retraction of a self-expanding stent in a body canal, which comprises an elongated tubular outer sleeve having disposed therein an elongated core which is movable relative to said sleeve and has a grip member formed at or near its distal end, which grip member is adapted to releasably hold a self-expanding stent within said outer sleeve.

24 Claims, 2 Drawing Sheets

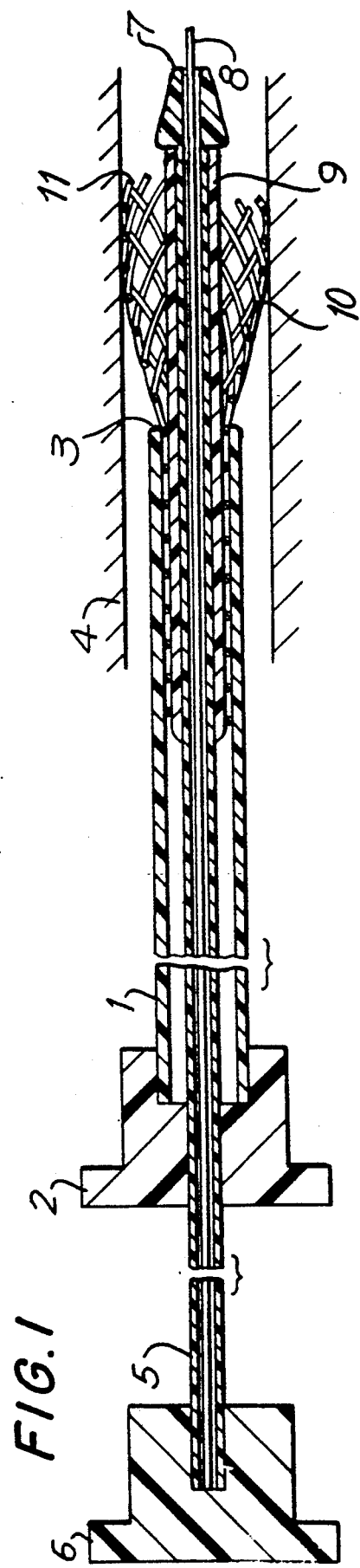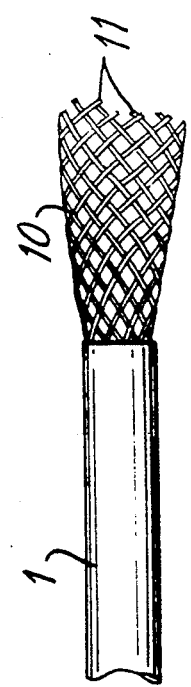

STENT PLACEMENT INSTRUMENT AND METHOD

This is a continuation of application Ser. No. 379,458, filed on July 13, 1989 abandoned.

BACKGROUND OF THE INVENTION

This invention relates to an instrument for the placement of a stent in a body canal and particularly to an instrument for the deployment or retraction of a self-expanding stent.

Tubular prostheses for transluminal implantation in body canals, for example blood vessels, for the purpose of repair or dilation are known in the art. These prostheses, referred to herein as stents, may be tubular elements which are non-extendible or extendible (i.e. adapted to extend longitudinally), or they may be self-expanding in the transverse direction.

A typical self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. The disclosure in U.S. Pat. No. 4,665,771 is incorporated herein by reference.

Placement of the stent according to U.S. Pat. No. 4,665,771 in a body vessel is achieved in one embodiment by a device which comprises the use of a piston or, in another embodiment, by use of latch means to push the stent forward.

U.S. Pat. No. 4,768,507 discloses a stent insertion apparatus which includes an inner core member with a spiral groove formed on its outer surface, which groove cooperates with an outer sheathing to form a spiral cavity adapted to contain an expandable coil stent. The coil stent is held in a radially compressed state within said spiral cavity by exerting a radial outward force on the outer sheath. The outer surface of the inner core member is slidably mounted within the hollow outer sheath cylinder so that the spiral cavity is adapted to contain only the coil stent for which it is designed. U.S. Pat. No. 4,743,152 discloses a device for implantation of a substantially tubular, radially expandable prosthesis including in combination said radially expandable prosthesis surrounding and concentric with a flexible probe and means for maintaining said prosthesis in a radially contracted state and for releasing said expandable prosthesis, wherein said means for maintaining and releasing the prosthesis comprises a hose concentrically surrounding said probe with one end of said hose being connected to the probe, the hose being folded inside itself, a double-walled section of said hose formed by said hose being folded inside itself, said double-walled section radially surrounding the prosthesis, a fluid-tight chamber provided between and defined by said probe and said hose, means for introducing and pressurizing a fluid in said chamber to reduce contact pressure and friction between said double-walled section of the hose, the prosthesis being released from the hose by axial relative movement of said one end of the hose with respect to an opposite end of said hose, said opposite end of said hose connected to an element of said device. The requirement that a chamber formed by a folded hose or outer sheath requires to be inflated with a pressurized fluid makes the device cumbersome and awkward to operate.

It has now been found that a self-expanding braided stent, such as that disclosed in U.S. Pat. No. 4,665,771, may be not only deployed into a body canal but also retracted back into the outer sleeve of a placement instrument which is simple, reliable and inexpensive if said instrument has the configuration and features as hereinafter described.

SUMMARY OF THE INVENTION

In accordance with the present invention there is provided an instrument for the deployment or retraction of a self-expanding braided stent in a body canal, which comprises an elongated tubular outer sleeve having a proximal end and a distal end, an elongated core disposed within said sleeve and movable relative to said sleeve, said core being longer than said sleeve and having a proximal end and a distal end and including a grip member at or near said distal end of the core, said grip member being an integral portion of the core or a sleeve or coating attached around the periphery of the core and being adapted to: (i) releasably hold a self-expanding stent within said outer sleeve, there being sufficient clearance between said grip member and said outer sleeve to accommodate said stent without distortion, (ii) deploy said stent beyond the distal end of said outer sleeve when said outer sleeve is moved in a backward direction relative to said core and (iii) retract said stent back within said outer sleeve when said core is pulled in a backward direction relative to said outer sleeve.

The invention also provides a method for the deployment of a self-expanding braided stent in a body canal, wherein said stent is pre-located on a grip member of a core within an outer sleeve of an instrument as described above so that the inner surface of the stent is releasably held by the outer contact surface of said grip member, which method comprises passing said instrument into the body canal until it reaches a position for proper placement of the stent and deploying the stent at said position by moving the outer sleeve proximally relative to the core, and withdrawing said instrument when the stent is properly located at the desired position in the body canal.

DETAILED DESCRIPTION OF THE INVENTION

The type of stent to be deployed or retracted by an instrument according to the invention is preferably a self-expanding braided stent such as that disclosed and illustrated in U.S. Pat. No. 4,655,771 and the invention will be particularly described hereinafter with reference to such a stent. However, it is to be understood that the instrument according to the invention may be used for the placement of any expansible stent having a configuration and dimensions which enable it to be releasably held between the grip member and outer sleeve of said instrument.

In a preferred embodiment of the invention the core is hollow and this feature assists in the proper positioning of the instrument in a body canal. Thus it is possible to pass a guide wire into and along the body canal and pass the instrument over the guide wire until it is properly positioned in the body canal. In this embodiment the instrument includes an elongated, flexible, steerable guide wire located within and along the axis of the core. When the instrument is positioned in the body canal the guide wire may be retained within the instrument until the stent is deployed at the desired location and withdrawn together with the instrument or, alternatively the guide wire may be withdrawn prior to deployment of the stent so that correct positioning of the stent, while still within the instrument, may be verified, for example, by endoscopic or fluoroscopic means.

To facilitate movement of the core relative to the outer sleeve, the core preferably has a handle attached to its proximal end and the proximal end of the outer sleeve preferably terminates in a flange or handle.

It is to be understood that, as used herein, the term "proximal" means the end or part nearest to the operator of the instrument and the term "distal" means the end or part furthest from the operator. Thus the front end of the instrument which enters the body canal is the distal end.

The most significant feature of the instrument according to the invention is the grip member and the significance of this feature is that it enables both deployment and retraction of the stent. In particular, the grip member is directly associated or integral with the core and is adapted to releasably hold a self-expanding stent within the outer sleeve. Thus, the grip member may be a sleeve or coating attached around the periphery of the core, an integral portion of the core or a length of the core having a larger outer diameter than the remainder of the core.

Preferred embodiments include an instrument in which the grip member is a sleeve of material with a friction contact surface or a sleeve of material that will take a set, for example a silicone rubber or a polyurethane. In each of these embodiments the sleeve material may have an outer surface which is substantially smooth and unbroken or an outer surface which is roughened or irregular. Alternatively, if the core itself is made from a material that will take a set the grip member may be an integral portion of the core. An advantage of this embodiment is that the grip member need not be a separate element which has to be attached or bonded to the core.

As used herein the term "friction" or "high friction" as applied to a material or its surface is intended to mean a material having a high coefficient of friction, i.e. a material whose surface offers high resistance to sliding motion; and the term "low friction" is intended to mean a material with a surface which offers little resistance to sliding motion and is relatively slippery.

Accordingly, since an important characteristic of the grip member is that it should be capable of gripping or holding a stent and this capability must be effective while the stent is retained within the instrument so that there is no slippage when the core is moved forward or backward relative to the outer sleeve, it is necessary when the grip member is a sleeve of material, that said material has a surface which offers high resistance to sliding motion. When the material is one which already has a high coefficient of friction the surface thereof which is in contact with the stent may be substantially smooth and unbroken. However, to increase the friction or enhance the inherent friction, the outer surface of the grip member may be roughened or irregular.

In an alternative embodiment of the invention the gripping characteristic of the grip member may be achieved when the grip member comprises a coating of a releasable adhesive. In this embodiment the adhesiveness of the coating must be sufficient to retain or grip the stent without slipping while it is still within the instrument but weak enough to allow the stent to be released, by its own expansion, when it is free from the constraint of the outer sleeve.

In a further embodiment of the invention the core itself is made from a high friction material, for example, a polyurethane, and the grip member comprises a length of said core, at or near the distal end of the core, having a larger outer diameter than the remainder of the core. In practice, the enlargement of diameter may be relatively small, of the order of about 0.01 inch, but it has been found that mounting the stent on this thicker portion of the core provides sufficient grip to enable the instrument to be operated as desired.

When the core itself is made from a material that will take a set, such a material being inherently of high friction, the larger diameter may not be necessary for the formation of the grip member. A "material that will take a set" is defined herein as a material that will be locally deformed in situ by the compression of the stent when it is pressed against the core by the outer sleeve and will retain the deformation so that the stent is effectively gripped thereby.

In each of the above-described embodiments the grip member preferably is at least as long as the stent.

When an expandable stent to be deployed by an instrument according to the invention is made from a plurality of cross threads, for example, plastic or metal filaments, and particularly metal filaments, such as by the braiding operation described in U. S. Pat. No. 4,655,771, the ends of the stent will have a number of exposed filament ends. To avoid snagging of these exposed ends, for example, into the wall of the outer sleeve, and to avoid consequential damage either to the outer sleeve or to the stent itself, it is advantageous to provide circumferential gaps adjacent the distal end and proximal end of the grip member to accommodate the respective ends of the stent. In this embodiment the ends of the stent tuck into said gaps thereby protecting them and preventing exposed filaments from snagging.

In contrast to the high friction characteristic of the grip member it is desirable that the inner wall of the outer sleeve has a low coefficient of friction to provide slidability and ease of movement of the stent-bearing grip member within the instrument. To achieve this characteristic it is preferable that the outer sleeve is a hollow catheter made from a low friction material, for example, a fluorocarbon polymer such as polytetrafluoroethylene.

Furthermore, to avoid the snagging problem mentioned above, it may be advantageous to provide the inner surface of the outer sleeve with a layer of hardened material. Such material also should be a low friction material.

Additionally, when the outer sleeve is made from a relatively soft material, the soft distal end thereof may have a protective hard hollow cap, for example, made of metal, attached thereto.

To facilitate proper placement of the instrument, it is advantageous to include one or more marker elements, each located at a predetermined position on the outer sleeve or core. In a preferred embodiment, each of said marker elements may be a band of metal or radiopaque material attached to the periphery of the outer sleeve, whereby correct placement of the instrument prior to deployment of the stent may be checked by fluoroscopy.

The above features or any combination thereof may be included in the instrument to provide smooth operation, proper placement and avoidance of snagging or damage to the stent.

In order to facilitate passage of the instrument into and along a body canal it also is advantageous to attach a flexible filiform to the distal end of the core. This embodiment also may avoid the use of a guide wire.

BRIEF DESCRIPTION OF THE DRAWINGS

Preferred embodiments of the invention are illustrated in the accompanying drawings in which:

FIG. 1 is a side elevation, partly in section, of an instrument according to the invention;

FIG. 2 is an enlarged side elevation of the distal end of an instrument showing a partly deployed stent;

DESCRIPTION OF PREFERRED EMBODIMENTS

Figure 3:
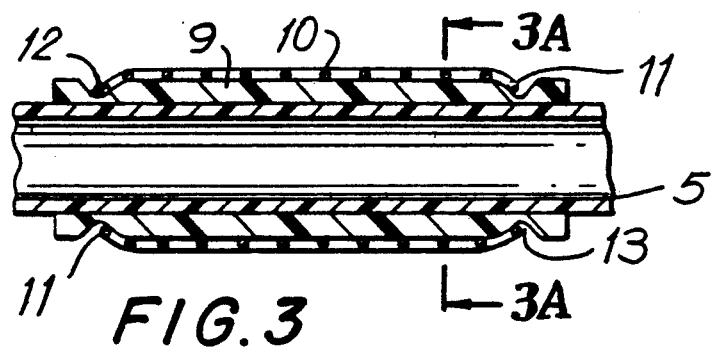
FIG. 3 is an enlarged cross section of one embodiment of a grip member.

The preferred embodiment of the invention illustrated in FIG. 1 of the drawings comprises an outer sleeve 1 having an integral handle 2 at its proximal end. The distal end 3 of the outer sleeve is positioned within a body canal 4. Disposed axially within the outer sleeve is a hollow core 5 having a handle 6 at its proximal end. The distal end 7 of the core has a stepped up diameter where it meets the distal end of the outer sleeve so that it provides a smooth transition from said end of the outer sleeve, and is also within the body canal. A guide wire 8 passes axially through the hollow core. Attached around the periphery of the core at its distal end is a grip member 9 which releasably grips a self-expanding stent 10, shown here partly deployed at the proper location within the body canal.

FIG. 2 is an enlarged side elevation showing a braided self-expanding stent 10, partly deployed from the distal end of the outer sleeve 1. This view shows the exposed ends of the wire filaments 11 which make up the stent.

Figure 3A:
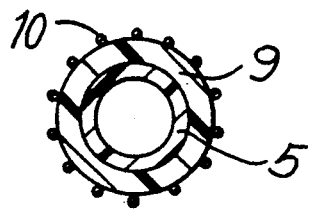
FIG. 3A is a cross-section through line 3A—3A on FIG. 3.

FIGS. 3 and 3A illustrate a grip member 9 made from a high friction material attached around the periphery of a hollow core 5. The grip member has circumferential gaps 12, 13 adjacent its distal end and proximal end, respectively, which accommodate the ends 11 of the stent, thereby avoiding snagging into the inner wall of the outer sleeve.

Figure 4:
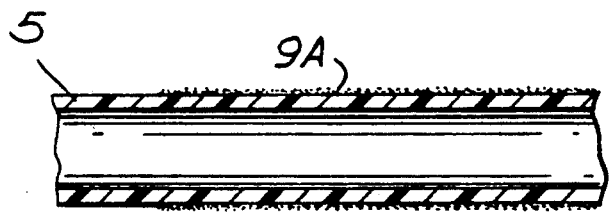
FIG. 4 and FIG. 5 are cross-sections of alternative grip members.

FIG. 4 illustrates a grip member 9A which comprises a coating of releasable adhesive around the periphery of the inner core 5.

Figure 5:
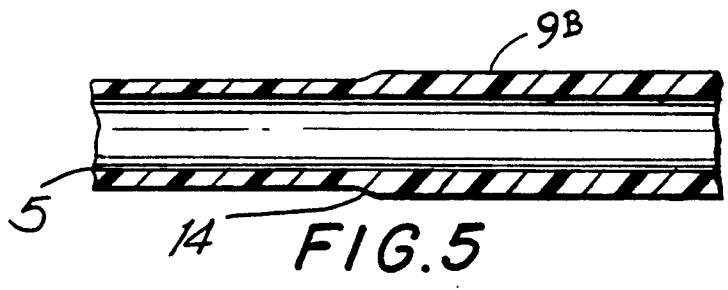

FIG. 5 illustrates, in cross-section, an embodiment in which the hollow core 5, is made from a high friction material, for example, a polyurethane, and the grip member 9B comprises a length of said core having a larger diameter than the remainder of the core, indicated schematically by the step 14. If said high friction material is a material that will take a set the grip member may be simply a portion of the core without the enlargement of diameter (not shown).

Figure 6:
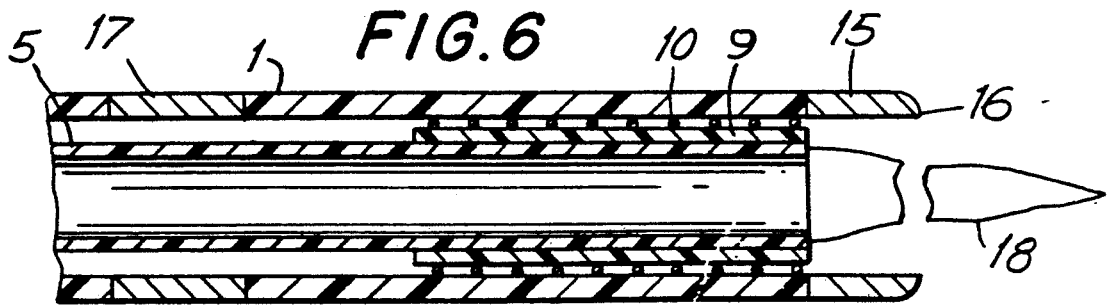
FIG. 6 is a side elevation of part of an instrument according to the invention showing other features.

FIG. 6 is a side elevation, partly in section, of part of an embodiment showing additional features. In this embodiment the outer sleeve 1, preferably made from polytetrafluoroethylene, has a smooth metal rim 15 at its distal end to prevent snagging from the ends of the stent 10. Preferably the distal end 16 of the metal rim is rounded to facilitate passage along the body canal.

Additionally, the metal cap may serve as a marker element for fluoroscopic monitoring of the placement of the instrument within the body canal. Additional or alternative marker elements 17 may be provided at pre-determined positions on the outer sleeve and/or on the core (not shown).

A flexible filiform 18 may be attached to the distal end of the core 5 to facilitate passage of the instrument along a body canal in known manner.

Deployment of a stent within a body canal in accordance with the method of the invention may be performed by using any of the embodiments illustrated in the drawings and described above.

To perform the method a self-expanding stent is introduced into the instrument in a manner known in the art and pre-located on the grip member. The grip member bearing the stent is withdrawn into the instrument so that the whole of the stent is within the outer sleeve, close to the distal end thereof, and is constrained by said outer sleeve. The instrument containing the stent is then introduced into the body canal, with or without the aid of a guide wire, and passed into the canal until it reaches a position for proper placement of the stent. The introduction and passage of the instrument in the body canal may be facilitated when a filiform is attached to the distal end of the core as described hereinabove.

The positioning of the instrument within the body canal may be monitored and verified by any means known in the art, for example, by use of an endoscope or by fluoroscopy. To assist fluoroscopic examination, one or more marker elements may be located at a predetermined position on the outer sleeve or core as described hereinabove.

When the correct position for proper placement of the stent is reached and verified, the stent is then deployed by moving the outer sleeve relative to the core. This operation is performed by holding the handle at the proximal end of the core so that the core, together with the grip member holding the stent, remains stationary, gripping the handle at the proximal end of the outer sleeve and withdrawing the latter towards the core handle so that the outer sleeve moves backward, thus exposing the stent, which, free from the constraint of the outer sleeve, expands to its expanded state. Before the stent is completely deployed from the instrument, the positioning thereof in the body canal is checked. If the position is correct then the withdrawal of the outer sleeve is continued until the stent is clear of the instrument and the instrument is then withdrawn from the body canal. However, if the monitoring reveals that the stent is not in its proper position then it may be retracted back within the outer sleeve simply by moving the core backwardly relative to outer sleeve using the handles on the core and outer sleeve. The instrument, containing the retracted stent, then may be re-positioned as required and the deployment operation repeated with the stent in its correct position.

Deployment of the stent by withdrawing the outer sleeve relative to the core has the advantage that it avoids the problem of the distal end of the stent digging into or snagging against the wall of the body canal, which problem might occur if the stent were to be pushed into the body canal from behind.

The capability of being able to retract the stent so that the instrument may be repositioned without damage to the stent or injury to the body canal is a distinct advantage of the present invention.

We claim:

1. In combination, a self-expanding braided stent and an instrument for the deployment or retraction of said stent in a body canal, which comprises an elongated tubular outer sleeve having a proximal end and a distal end, an elongated core disposed within said sleeve and movable relative to said sleeve, said core being longer than said sleeve and having a proximal end and a distal end and including a grip member at or near said distal end of the core, said grip member being an integral portion of the core or a sleeve or coating attached around the periphery of the core and being adapted to: (i) releasably hold said self-expanding stent within said outer sleeve, there being sufficient clearance between said grip member and said outer sleeve to accommodate said stent without distortion, (ii) deploy said stent beyond the distal lend of said outer sleeve when said outer sleeve is moved in a backward direction relative to said core and (iii) retract said stent back within said outer sleeve when said core is pulled in a backward direction relative to said outer sleeve.

2. The combination according to claim 1, in which said core is hollow.

3. The combination according to claim 2, which includes an elongated flexible, steerable guide wire located within and along the axis of said core.

4. The combination according to claim 1, in which said core has a handle attached to its proximal end to facilitate movement at the core relative to the outer sleeve.

5. The combination according to claim 1, in which the proximal end of said outer sleeve terminates in a flange or handle to facilitate movement of the outer sleeve relative to said core.

6. The combination according to claim 1, in which said grip member is a sleeve of material with a friction contact surface.

7. The combination according to claim 1, in which said grip member is made from a material that will take a set and is either an integral portion of said core or a sleeve attached around the periphery of the core.

8. The combination according to claim 7, in which said material is a silicone rubber or a polyurethane.

9. The combination according to claim 1, in which said grip member comprises a coating of a releasable adhesive.

10. The combination according to claim 1, in which said grip member is a sleeve of material having an outer surface which is substantially smooth and unbroken.

11. The combination according to claim 1, in which said grip member is a sleeve of material having an outer surface which is roughened or irregular.

12. The combination according to claim 1, in which said core is made from a high friction material and said grip member comprises a length of said core having a larger outer diameter than the remainder of the core.

13. The combination according to claim 12, in which said high friction material is a polyurethane.

14. The combination according to claim 1, in which said grip member is at least as long as said stent.

15. The combination according to claim 1, which includes one or more marker elements, each located at a predetermined position on the outer sleeve or core.

16. The combination according to claim 15, in which each of said marker elements is a band of metal or radiopaque material attached to the periphery of the outer sleeve.

17. The combination according of claim 1, in which said outer sleeve is a hollow catheter made from a low friction material.

18. The combination according to claim 17, in which said low friction material is polytetrafluoroethylene.

19. The combination according to claim 17, in which the inner surface of the catheter has a layer of hardened material to prevent damage by the ends of the stent.

20. The combination according to claim 17, in which the soft distal end of the catheter has a protective hard hollow rim attached thereto.

21. The combination according to claim 20, in which said rim is made of metal.

22. The combination according to claim 1, in which said grip member is provided with circumferential gaps adjacent its distal end and proximal end to accommodate the ends of the stent.

23. The combination according to claim 1, in which a flexible filiform is attached to the distal end of the core.

24. A method for the deployment of a self-expanding braided stent in a body canal, wherein said stent is prelocated on a grip member of a core within an outer sleeve of a instrument according to claim 1 so that the inner surface of the stent is releasably held by the outer contact surface of said grip member, which method comprises passing said instrument into the body canal until it reaches a position for proper placement of the stent and deploying the stent at said position by moving the outer sleeve proximally relative to the core, and withdrawing said instrument when the stent is properly located at the desired position in the body canal.

* * * * *